United States Patent

Sheridan

[11] Patent Number: 4,459,255
[45] Date of Patent: Jul. 10, 1984

[54] CATHETER DISTAL END FINISHING METHOD

[76] Inventor: David S. Sheridan, Rte. 5, Argyle, N.Y. 12809

[21] Appl. No.: 437,441

[22] Filed: Oct. 18, 1982

[51] Int. Cl.³ ............................................. B29C 17/00
[52] U.S. Cl. .................................... 264/102; 264/1.5; 264/320; 264/571; 425/388; 425/812
[58] Field of Search ................ 264/1.5, 2.7, 102, 320, 264/571, 322; 425/812, DIG. 218, 388, 392, 393

[56] References Cited

U.S. PATENT DOCUMENTS

| | | | |
|---|---|---|---|
| 2,976,571 | 3/1961 | Moslo | 425/812 |
| 3,725,522 | 4/1973 | Sheridan et al. | 264/296 |
| 4,165,062 | 8/1979 | Mitchell | 425/812 |
| 4,174,241 | 11/1979 | Rockar et al. | 264/102 |
| 4,215,087 | 7/1980 | Mathison | 264/320 |
| 4,292,270 | 9/1981 | Hannah et al. | 264/320 |

Primary Examiner—James B. Lowe
Attorney, Agent, or Firm—Carroll F. Palmer

[57] ABSTRACT

The distal ends of plastic catheters are finished to form smoothly rounded tips by forcing the distal ends into a heated cup-like mold and at the same time applying suction to the central lumen of the catheter either via the proximal end of the lumen or via a raised central portion of the mold.

3 Claims, 2 Drawing Figures

CATHETER DISTAL END FINISHING METHOD

BACKGROUND OF THE INVENTION

1. Field of the Invention

The invention relates broadly to medico-surgical tube structures and methods of their manufacture. More particularly, it concerns methods for finishing the distal ends of medico-surgical tubes, especially catheters.

2. Description of the Prior Art

Catheter distal end tips should not have sharp corners, sharp points, ragged edges or any other injury causing features. Manufacturers have either hand finished or molded the tips to eliminate such problems. Molding in heated cavities has become the common method (see U.S. Pat. No. 3,725,522).

One problem associated with the molding method is the trapping of air in and around the molten plastic at the bottom of the heated mold. As the tube is forced down into the mold, air becomes compressed ahead of it much the same as a piston being forced into a cylinder. If there is no means for the air to escape, it prevents the plastic from taking the shape of the mold, or some air may become trapped within the plastic as a bubble or blister.

Two methods are commonly used to deal with the air trapping problem. One is to provide a bleed hole to let the air escape (see U.S. Pat. Nos. 3,725,522 and 4,292,270). A second is to provide enough clearance around the tube and the mold cavity so air can escape back up the cavity. However, by doing either of these, new problems can be created.

In the bleed hole method, while the hole allows the softened plastic to take the shape of the mold, some plastic may be extruded through the bleed hole. When the tube is then removed from the mold, it is left with a projection or other evidence where the bleed stringer has broken off. If the second method is used, it is possible that the molten plastic can be forced back up the clearance space. This can produce a flap or ridge which is undesireable.

OBJECTS

A principal object of this invention is the provision of new methods for the finishing of the ends of medico-surgical tubes. Further objects include the provision of:

1. New methods for creating smooth tips on the distal ends of catheters without the simultaneous production of sprue projections or flash.

2. A new technique for eliminating the trapped air problem in the finishing of the distal ends of catheters by forcing the distal end into a heated mold.

Other objects and further scope of applicability of the present invention will become apparent from the detailed description given hereinafter; it should be understood, however, that the detailed description, while indicating preferred embodiments of the invention, is given by way of illustration only, since various changes and modifications within the spirit and scope of the invention will become apparent to those skilled in the art from this detailed description.

SUMMARY OF THE INVENTION

These objects are accomplished according to the present invention by a method of finishing the distal end of a plastic catheter having a major central lumen which comprises providing a cup-like mold contoured to the shape desired for the finished distal end including a raised central portion to project into the catheter's central lumen when it is inserted in the mold, heating the mold to a temperature above the plastic flow temperature of the catheter, forcing the distal end of the catheter into the mold, and simultaneously applying suction to the central lumen of the catheter.

In one preferred embodiment of the invention the suction is applied to the proximal end of the catheter lumen. In another embodiment, the suction is applied through a raised central portion of the mold.

BRIEF DESCRIPTION OF THE DRAWINGS

A more complete understanding of the invention may be had by reference to the accompanying drawings in which.

DESCRIPTION OF THE PREFERRED EMBODIMENTS

Figure 1:
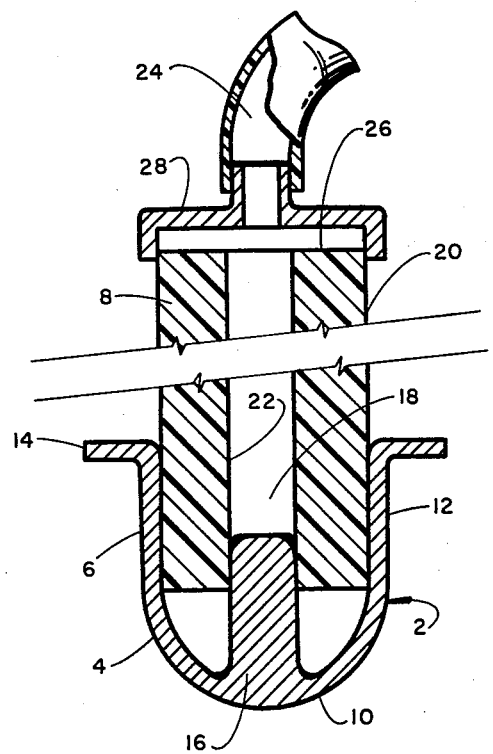
FIG. 1 is a sectional view showing the finishing of the end of a catheter in a mold of the invention in accordance with one embodiment of the invention.

Referring in detail in the drawings and, in particular, in FIG. 1, the molding device 2 comprises a cup-like mold 4 contoured to the shape desired to be formed in the distal end 6 of the catheter 8. The contour of the mold 4 includes the tube tip shaping bottom 10, sidewall 12 and entrance lip 14.

The mold 4 further comprises a raised central portion 16 designed to project into the central lumen 18 of the catheter 8 when it is inserted into the mold 4. The portion 16 in the embodiment of FIG. 1 is in the form of a solid pin, but it may instead be in the form of a hollow tube closed at the top.

The clearances between the catheter walls 20 and 22 and the surfaces of the mold sidewalls 12 and the central portion 16, respectively, are designed close enough so that the catheter 8 can be inserted without interference, but not with clearance to the extent that molten plastic can flow back up the inside of wall 12 or the outside of central portion 16.

The molding device 2 includes suction tube 24 provided with a cap 26 to fit over the proximal end 28 of the catheter lumen 18. A typical cycle for finishing the catheter 8 in the molding device 2 is as follows: The catheter distal end 6 is inserted into the entering portion of the mold cavity. The suction tube 24 is connected to a vacuum source (not shown) and the finishing cycle is initiated by applying a suction to the tube 24 from the vacuum source, e.g., with a vacuum potential of 22" to 29" Hg. This produces a suction on the inside of the catheter 6. Such applied suction draws the catheter toward the bottom 10 of the mold 4. The cycle is programmed so that the mold bottom 10 will be heated when the suction is applied, or heating of the mold may be delayed a predetermined amount. Downward pressure on the catheter is applied by hand or this may be done by electrical, mechanical or fluid pressure devices (not shown). The combination of downward pressure on the catheter forcing it toward the bottom 10 of the mold 4 plus the application of the heat bringing the plastic to a flowing (molten) condition and evacuation of any air that may, in the absence of the suctioning, become entrapped between the catheter and the mold, permits the flowing plastic to fully fill the mold bottom 10 to form the desired shape on the catheter tip without sprue projections, flash or the like.

Suction need only be applied during the part of the finishing cycle when the catheter is advancing downward to the mold bottom 10 with the plastic of the catheter heated to flowable condition. During the period of cooling, heat and vacuum are removed, but the downward pressure on the catheter is advantageously continued through the cooling stage of the finishing cycle.

Figure 2:
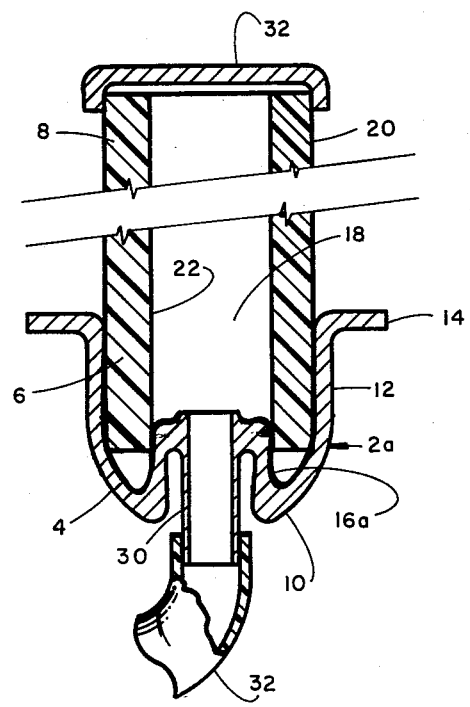
FIG. 2 is a sectional view showing the finishing of the end of a catheter in accordance with another embodiment of the invention.

The molding device 2A of FIG. 2 is essentially like that of FIG. 1. except for the central portion 16A which is of tubular form that includes an integral outlet tube 30. In the finishing cycle using the device 2A, the tube 30 is connected via hose 32 to the vacuum source (not shown) and the proximal end 20 of catheter 8 is closed with a cap 32. Suction is applied via the tube 30 in the initial stage of the finishing cycle as contrasted to its application via tube 24 in the molding device 2. Otherwise the finishing operation parallels that described for device 2.

In the foregoing description, only one catheter tip configuration is illustrated, but it should be understood that a variety of different tip shapes may be made by the new finishing methods.

The embodiments of the invention in which an exclusive property or privilege is claimed are defined as follows:

1. A method of finishing the distal end of a plastic catheter having a major central lumen which comprises:
   providing a cup-like mold contoured to the shape desired for said finished distal end including a raised central portion to project into said central lumen when a catheter is inserted in said mold,
   heating said mold to a temperature above the plastic flow temperature of said catheter,
   forcing said distal end of said catheter into said mold, and
   simultaneously applying suction to said central lumen of said catheter.

2. The method of claim 1 wherein said suction is applied to the proximal end of said catheter lumen.

3. The method of claim 1 wherein said suction is applied through said raised central portion of said mold.

* * * * *